(12) United States Patent
Jin et al.

(10) Patent No.: US 9,289,457 B2
(45) Date of Patent: Mar. 22, 2016

(54) **COMPOSITION FOR PREVENTING OR TREATING LIVER DISEASES, CONTAINING PLANT STEM CELL LINES DERIVED FROM THE CAMBIUM OF *PANAX GINSENG* INCLUDING MOUNTAIN GINSENG OR GINSENG AS ACTIVE INGREDIENT**

(71) Applicant: UNHWA Corporation, Jeonju, Jeollabuk-Do (KR)

(72) Inventors: Young Woo Jin, Jeonbuk (KR); Eun Kyong Lee, Jeonbuk (KR); Min Jung Lim, Jeonbuk (KR)

(73) Assignees: UNHWA COPRORATION, Jeonju-Si, Jeollabuk-Do (KR); Young Woo Jin, Jeonju-Si, Jeollabuk-Do (KR); Eun Kyong Lee, Jeonju-Si, Jeollabuk-Do (KR)

( * ) Notice: Subject to any disclaimer, the term of this patent is extended or adjusted under 35 U.S.C. 154(b) by 362 days.

(21) Appl. No.: 13/863,829

(22) Filed: Apr. 16, 2013

(65) Prior Publication Data
US 2013/0202631 A1 Aug. 8, 2013

Related U.S. Application Data

(63) Continuation of application No. 13/058,949, filed as application No. PCT/KR2009/004563 on Aug. 14, 2009, now abandoned.

(30) Foreign Application Priority Data

Aug. 14, 2008 (KR) .......................... 10-2008-0080124

(51) Int. Cl.
| *A61K 36/00* | (2006.01) |
| *A61K 36/258* | (2006.01) |
| *A61K 36/25* | (2006.01) |
| *A01H 4/00* | (2006.01) |
| *A23L 1/30* | (2006.01) |
| *C12N 5/04* | (2006.01) |

(52) U.S. Cl.
CPC .............. *A61K 36/258* (2013.01); *A01H 4/005* (2013.01); *A23L 1/3002* (2013.01); *A61K 36/25* (2013.01); *C12N 5/04* (2013.01)

(58) Field of Classification Search
None
See application file for complete search history.

(56) References Cited

U.S. PATENT DOCUMENTS

| 4,795,742 | A | 1/1989 | Liu |
| 8,017,397 | B2 | 9/2011 | Jin et al. |
| 8,053,238 | B2 | 11/2011 | Jin et al. |
| 8,247,230 | B2 | 8/2012 | Jang et al. |
| 2010/0255585 | A1 | 10/2010 | Yu et al. |
| 2010/0272692 | A1 | 10/2010 | Park et al. |
| 2011/0097310 | A1 | 4/2011 | Jang et al. |
| 2011/0117039 | A1 | 5/2011 | Lee et al. |
| 2011/0229443 | A1 | 9/2011 | Jin et al. |
| 2012/0189660 | A1 | 7/2012 | Jin et al. |

FOREIGN PATENT DOCUMENTS

| JP | 04005235 A | * | 1/1992 |
| KR | 20010057525 A | | 7/2001 |
| KR | 100448552 B1 | | 9/2004 |

OTHER PUBLICATIONS

Yun, T.—K.; "Panax ginseng—a non-organ-specific cancer preventive?" The Lancet Oncology, 2001, pp. 49-55, vol. 2.
Attele, A. A., et al.; Ginseng Pharmacology, Multiple Constituents and Multiple Actions, Biochemical Pharmacology, 1999, pp. 1685-1693, vol. 58.
International Search Report, Apr. 2, 2010.
Liver Disease from Wikipedia, Accessed on Nov. 14, 2012, pp. 1-3.
Davis, et al., "Preventing hepatitis C: 'common sense,' 'the bug' and other perspectives from the risk narratives of people who inject drugs," Social Science & Medicine, 1982, pp. 1807-1818, vol. 59.
Fest et al., "Rish factors associated with hepatitis B or C markers or elevated alanine aminotransferase level among blood donors on a tropical island: the Guadeloupe experience," Transfusion, 1992, pp. 760-763, vol. 32.
Aggarwal, et al., "Hepatitis E vaccine," Hepatology International, 2008, pp. 308-315, vol. 2.
Daily, et al., "IGIV:a potential role for hepatitis B prophylaxis in the bone marrow peritransplant period." Bone Marrow Transplantation, 1998, pp. 739-742, vol. 21.
Lopez-Labrador, "Hepatitis C Virus NS3/4A Protease Inhibitors." Recent Patents on Anti-Infective Drug Discovery, 2008, pp. 157-167, vol. 3.

\* cited by examiner

*Primary Examiner* — Qiuwen Mi
(74) *Attorney, Agent, or Firm* — Tristan A. Fuierer; Moore & Van Allen, PLLC

(57) ABSTRACT

The present invention relates to a composition for preventing or treating liver diseases, which contains, as an active ingredient, any one or more of a homogeneous cell line derived from the cambium of *Panax ginseng*, including wild ginseng or ginseng, a lysate thereof, an extract thereof and a culture medium thereof. The homogeneous cell line according to the present invention, a lysate thereof, an extract thereof and a culture medium thereof have minimized side effects compared to existing agents for treating liver diseases, and thus are safe for the human body. Also, they can increase the levels of s-antibody (HBsAb) and e-antibody (HBeAb) against hepatitis virus and inhibit the proliferation of hepatitis virus, and thus they are useful for the prevention and treatment of liver diseases. In addition, they have the effect of lowering the levels of liver injury, and thus are useful as a functional food for improving liver function.

14 Claims, 2 Drawing Sheets

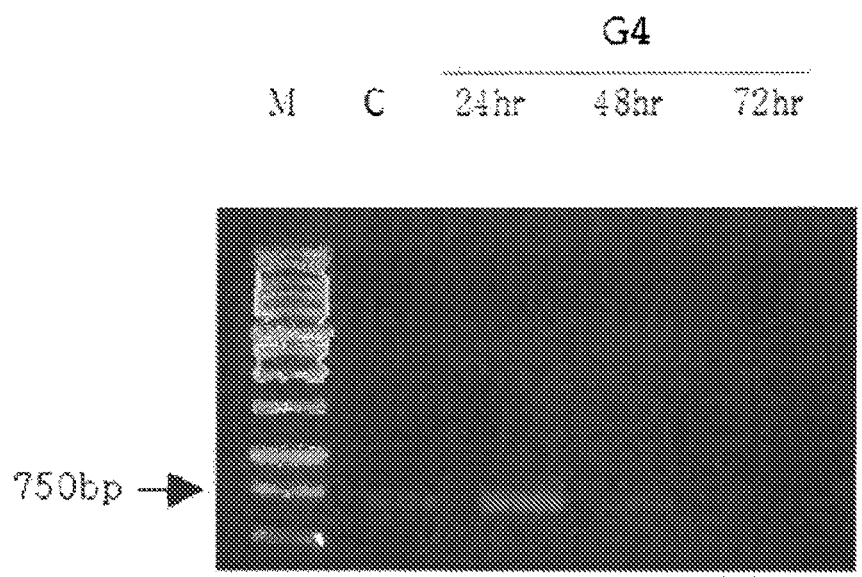

```
                          SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Synthetic Construct

<400> SEQUENCE: 1
gggggaattc atggagaaca tcacatcagg attc                              34

<210> SEQ ID NO 2
<211> LENGTH: 33
<212> TYPE: DNA
<213> ORGANISM: Artificial Sequence
<220> FEATURE:
<223> OTHER INFORMATION: Synthetic Construct

<400> SEQUENCE: 2
gggctgcagt taaatgtata cccaaagaca aaa                               33
```

COMPOSITION FOR PREVENTING OR TREATING LIVER DISEASES, CONTAINING PLANT STEM CELL LINES DERIVED FROM THE CAMBIUM OF *PANAX GINSENG* INCLUDING MOUNTAIN GINSENG OR GINSENG AS ACTIVE INGREDIENT

CROSS REFERENCE TO RELATED APPLICATIONS

This application is a continuation application of and claims the priority of U.S. patent application Ser. No. 13/058,949 filed on Apr. 4, 2011, entitled "COMPOSITION FOR PREVENTING OR TREATING LIVER DISEASES, CONTAINING PLANT STEM CELL LINES DERIVED FROM THE CAMBIUM OF PANAX GINSENG INCLUDING MOUNTAIN GINSENG OR GINSENG AS ACTIVE INGREDIENT" in the name of Young Woo Jin, et al., which claims priority of International Patent Application No. PCT/KR2009/004563 filed on 14 Aug. 2009, which claims priority of Korean Patent Application No. 10-2008-0080124 filed on 14 Apr. 2008, all of which are hereby Incorporated by reference herein in their entireties.

TECHNICAL FIELD

The present invention relates to a composition for preventing or treating liver diseases containing, as an active ingredient, any one or more of a cell line derived from the cambium of *Panax ginseng*, including wild ginseng or ginseng, or an extract thereof, a lysate thereof and a culture thereof.

BACKGROUND ART

These days, people are being exposed to the risk of various liver diseases due to excessive stress, drinking, smoking, environmental pollution, viruses, etc. Typical liver diseases include liver cirrhosis, alcoholic liver cirrhosis, fatty liver, toxipathic liver diseases, acute and chronic hepatitis, etc. Of these, hepatitis is a serious disease that spreads worldwide and is infectious at a low degree. Medical practitioners presume that 70-80% of liver cirrhosis and liver cancer patients are due to the worse of chronic hepatitis.

Particularly, hepatitis B virus (HBV) is a member of the Hepadnaviridae family which infects the human body and has an incubation period of about 60-110 days, and 90-95% of patients with hepatitis B virus completely recover from hepatitis B after various clinical stages. However, in the case of patients who did not recover from hepatitis B infection, HBV DNA is assimilated into the genomic DNA of human liver cells to cause chronic active hepatitis, liver cirrhosis, liver cancer and the like. Chronic hepatitis caused by HBV causes chronic viral infections, lymphoma diseases and chronic renal failure, like other diseases. Thus, chronic hepatitis is regarded as a highly lethal disease that develops into a more potent disease, leading to patient's death.

Thus, in order to treat viral hepatitis, various methods employing interferon, nucleic acid derivatives or immune modulators have been attempted. However, interferon-α reported to have a therapeutic effect did not show a continuous inhibitory effect, and patients caused by mother-to-infant vertical transmission of hepatitis virus shows resistance to interferon-α. Also, a drug that can completely cure hepatitis has not yet been developed, and in current therapy for hepatitis, an antiviral drug is continuously administered to prevent hepatitis from developing into a serious liver disease. However, it was reported that antiviral drugs cause viral mutations that induce resistance to the drugs and makes the drug effect impotent.

Thus, a current method for treating hepatitis is a passive method that inhibits the proliferation of virus to prevent hepatitis from developing into a serious liver disease, and a method of directly treating hepatitis by, for example, forming an antibody, has not yet been reported. Therefore, it has been required to develop a novel method for preventing and treating hepatitis.

Accordingly, the present inventors have made many efforts to develop a natural material-derived composition having excellent effects on the prevention and treatment of liver diseases, including hepatitis. As a result, the present inventors have found that a homogeneous cell line derived from the cambium of *Panax ginseng*, including wild ginseng or ginseng, a lysate thereof, an extract thereof and a culture thereof have excellent effects on the prevention and treatment of liver diseases, thereby completing the present invention.

DISCLOSURE OF INVENTION

It is an object of the present invention to provide a natural material-derived composition which has minimized side effects compared to existing agents for treating liver diseases and exhibits preventive and therapeutic activity against liver diseases.

To achieve the above object, the present invention provides a composition for preventing or treating liver diseases, which contains any one or more of a cell line, which is derived from the cambium of *Panax ginseng* and has the following characteristics, an extract thereof, a lysate thereof and a culture thereof:

(a) it is in an innately undifferentiated state;
(b) it is a homogeneous cell line; and
(c) it is morphologically characterized by multiple vacuoles.

The present invention also provides a functional food for improving liver function, which contains any one or more of said cell line, an extract thereof, a lysate thereof and a culture thereof.

The present invention also provides a composition for inhibiting the proliferation of hepatitis virus, which contains any one or more of said cell, line, an extract thereof, a lysate thereof and a culture thereof.

The present invention also provides an immune-enhancing agent for increasing the level of antibody against hepatitis virus, which contains any one or more of said cell line, an extract thereof, a lysate thereof and a culture thereof.

The present invention also provides the use of any one or more of said cell line, an extract thereof, a lysate thereof and a culture thereof for preventing or treating liver diseases.

The present invention also provides a method for preventing or treating liver diseases, which comprises a step of applying any one or more of said cell line, an extract thereof, a lysate thereof and a culture thereof.

Other features and embodiments of the present invention will be more apparent from the following detailed descriptions and the appended claims.

BRIEF DESCRIPTION OF THE DRAWINGS

In FIG. 2, M: 1 kb ladder marker; control; G4: a PBS extract of the homogeneous cell line according to the present invention; and G5: a PBS extract of the cultured root of wild ginseng.

FIG. 3 is an electrophoresis photograph showing the results of observing the hepatitis virus inhibitory effect of the homogeneous cell line of the present invention at various points of time. In FIG. 3, M: 1 kb ladder marker; C: control; and a PBS extract of the homogeneous cell line according to the present invention.

DETAILED DESCRIPTION AND BEST MODE FOR CARRYING OUT THE INVENTION

Figure 1:
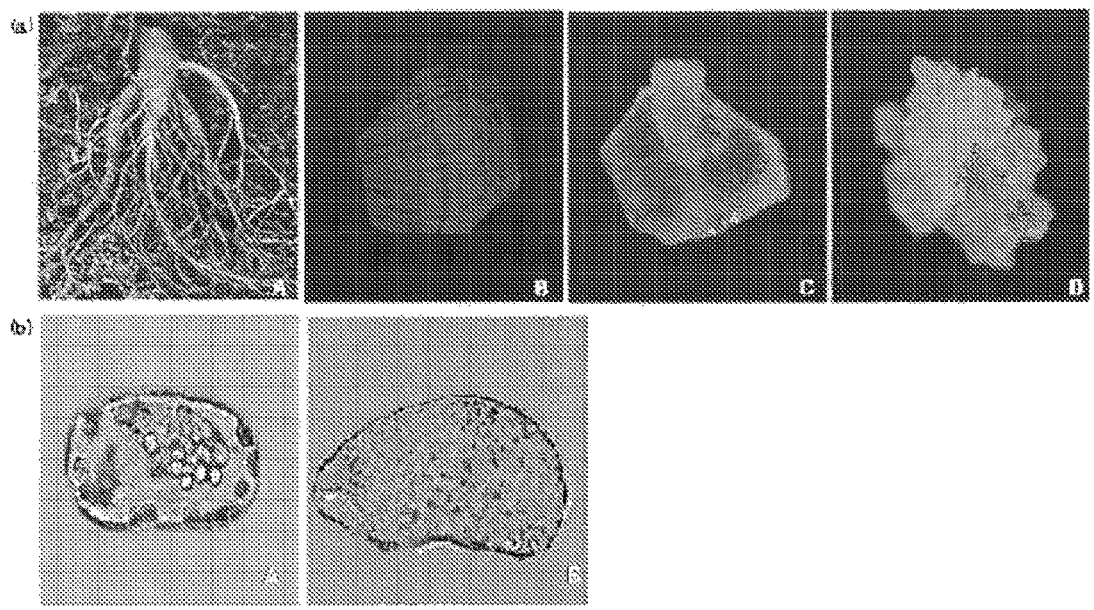
FIG. 1(*a*) is a set of photographs (A to D) showing a process of deriving a homogeneous cell line according to the present invention, and FIG. 1(*b*) is a set of photographs showing the results of observing a cambium-derived homogenous cell line (A) and a ginseng cotyledon-derived callus cell line (B) at a single cell level under an optical microscope.

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

The definition of main terms used in the detailed description of the invention is as follows.

As used herein, the term "cambium" refers to a tissue that thickens the stem and root to allow the plant to grow volumetrically. It was reported that when the cambium, a meristem where the most active cell division occurs, is used as an explant for plant tissue culture, rapid and mass production of cells is possible (Korean Patent Registration No. 10-0533120).

As used herein, the term "lysate" refers to a cell lysate obtained by disrupting cells through a chemical method with, for example, a detergent, or a physical method. The term "extract" of a cell line refers to a substance obtained by dissolving cells in a solvent and isolating the substance, and the extract can be concentrated through distillation or evaporation. In addition, the term "culture" of the cell line as used herein refers to a material containing a culture medium and/or a cultured cell line, wherein the cultured cell line is intended to include a cell line which differentiates under culture conditions or which have improved ability to produce and/or secrete useful substances.

As used herein, the term "innately undifferentiated" means that cells are not present in an undifferentiated state through a dedifferentiation process, but are originally maintained in a pre-differentiated state.

In one aspect, the present invention provides a composition for the prevention or treatment of liver diseases containing, as an active ingredient, any one or more of a cell line derived from the cambium of *Panax ginseng*, a lysate thereof, an extract thereof and a culture thereof. In the present invention, *Panax ginseng* includes wild ginseng or ginseng (Lian M. L. et al., *J. Plant Biology*, 45: 201, 2002; Han J. Y. et al., *J. Plant Biology*, 49:26, 2006; Teng W. L. et al., *Tissue and Organ Culture*, 68:233, 2002). In the present invention, the wild ginseng or ginseng includes outdoor-cultivated ginseng or tissue-cultured ginseng (adventitious root and adventitious root-derived cell line).

The *Panax ginseng* cambium-derived cell line according to the present invention, has the following characteristics: (a) it is in an innately undifferentiated state; (b) it is a homogeneous cell line; and (c) it is morphologically characterized by multiple vacuoles. The *Panax ginseng* cambium-derived cell line according to the present invention is additionally characterized in that: (a) it exists at single cell level during suspension culture; (b) it has low sensitivity to shear stress in a bioreactor compared to cell lines derived from tissues other than the cambium of *Panax ginseng*, and (c) it has a higher growth rate and can be cultured more stably compared to the cell lines than those cell lines derived from tissues other than the cambium of *Panax ginseng*.

The homogeneous cell line according to the present invention is obtained using an isolation method comprising the steps of (a) obtaining a tissue containing the cambium of *Panax ginseng*; (b) culturing the obtained cambium containing tissue in a medium containing indole-3-acetic acid (IAA) or indole-3-butyric acid (IBA), thereby inducing a cambium-derived cell line, wherein osmotic stress is applied to the cambium containing storage root before, during or after the culturing; and (c) collecting the induced cambium-derived cell line.

In the step (b), osmotic stress is applied to the obtained cambium-containing storage root tissue while the culture is performed or before or after the culture is performed.

In the present invention, the cell line is obtained by additionally performing a step of proliferating the obtained cambium-containing tissue in a medium containing one or more of 2,4-D (2,4-dichlorophenoxyacetic acid), picloram and IBA.

In the present invention, the culture of the cell line is obtained by additionally culturing the cell line in a medium, which, as elicitors, contains 3-5 wt % of raw sugar or sugar, and/or any one or more of methyl jasmonate, chitosan, phenylalanin, benzoic acid, ABA, salicylic acid and sodium acetate. Herein, the medium preferably contains 3-5 wt % of raw sugar or sugar and at least one substance selected from the group consisting of methyl jasmonate, fungal extract, bacterial extract, yeast extract, chitosan, glucomannan, glucan, phenylalanine, benzoic acid, salicylic acid, arachidonic acid, STS, mevalonalonate N-benzolyglycine, ABA, SNP, IPP, BHT, CCC, ethephon, hippuric acid, ammonium ceric nitrate, $AgNO_3$, vanadyl sulfate, p-aminobenzoic acid, brassinosteroids, sodium alginate, and sodium acetate.

Also, in the present invention, it is possible to use a culture obtained by stresses treating the cell line with elicitors, including light, photoperiod, shear, UV radiation, heat, ethylene, an antifungal agent, an antibiotic, heavy metal salt and high-concentration salt to apply physical and chemical thereto. In one embodiment of the present invention, a cell line culture applied with air stress as the elicitors was used.

The medium used in the present invention is a conventional medium for plant tissue culture, and examples thereof include, but are not limited to, N6 medium, SH medium, MS medium, AA medium, LS medium, B5 medium, WPM medium, LP medium, White medium, GD medium, DKW medium, DCR medium, etc.

In the present invention, the extract is preferably obtained using a solvent selected from the group consisting of distilled water, alcohol such as lower alcohol or the like, acetone, DMSO (dimethyl sulfoxide), and mixed solvents thereof. Herein, examples of the lower alcohol include alcohols having 1 to 5 carbon atoms, such as methanol and ethanol.

In the present invention, the liver disease is preferably any one selected from among hepatitis, liver cancer, liver cirrhosis, fatty liver and toxipathic liver disease.

In another aspect, the present invention relates to a composition for inhibiting the proliferation of hepatitis virus or an immune-enhancing agent for increasing the level of antibody against hepatitis virus, which contains any one or more of said homogeneous cell line, a lysate thereof, an extract thereof and a culture thereof.

In one Example of the present invention, the homogeneous cell line extract according to the present invention was administered to the HepG2.2.15 cell line in vitro, and whether HBV virions were produced was examined by PCR amplification. As a result, it was shown that an extract of the cultured root of wild ginseng had no inhibitory effect on the production of HBV virus, whereas the cell line extract according to the present invention inhibited the production of HBV virus.

Meanwhile, in another Example of the present invention, the homogeneous cell line according to the present invention was administered to a patient, and then HBsAg and HBeAg antigens, HBsAb, HBeAb and HBcAb antibodies and hepatitis B virus (HBV) DNA were quantitatively examined. As a result, it was found that s-antibody was formed, indicating complete recovery from hepatitis B, and also that hepatitis B antigens were reduced. During the replication of hepatitis B virus, three major antigens (c-, s- and e-antigens) are made, in which the c (core) antigen (HBcAg) is a structural antigenic determinant, and the s (surface) antigen (HBsAg) is an antigenic determinant that appears due to viral surface proteins. Of these antigens, the e-antigen (HBeAg) is an indicator of hepatitis B virus infection.

TABLE 1

| Antibody & Antigen | Indication | Normal Ranges |
| --- | --- | --- |
| Existence of s antigen (HBsAg) | Indicating hepatitis B | − |
| Existence of s antibody (HBsAb) | Indicating an infection of hepatitis B virus, but complete recovery from the hepatitis B | + |
| Existence of e antigen (HBeAg) | Indicating vigorous proliferation of hepatitis B virus | − |
| Existence of e antibody (HBeAb) | Indicating 90% recovery of hepatitis Inspite of the existence of e antibody, DNA test is needed due to a mutation of hepatitis B virus | + |
| HBV-DNA | Indicating the existence and activity of virus | − |

* Formation of immunity to hepatitis B (the Health Promotion Center, the Korea Association of Health Promotion)
※ HBs Ag(EIA): 0-2.53 (negative), and 2.54 or more (positive)
※ HBs Ab(EIA): 0-14.9 (negative), and 15.0 or more (positive).

Namely, it was confirmed through the above Examples that the ginseng cambium-derived homogeneous cell line according to the present invention has the effects of preventing and treating hepatitis. Also, it was confirmed that the ginseng cambium-derived homogeneous cell line according to the present invention increases not only the level of s-antibody, but also the level of e-antibody, suggesting that the homogenous cell line according to the present invention has an immune-enhancing effect of increasing the level of antibody against hepatitis virus.

Accordingly, it was found as described above that the homogeneous cell line according to the present invention, an extract thereof and a culture have preventive and therapeutic activity against liver diseases. Thus, even though in the present invention, there is no specific example showing that the composition containing a lysate of the homogenous cell line shows the effects of preventing and treating liver diseases, it will be obvious to those skilled in the art that the composition containing the homogeneous cell line lysate according to the present invention can also show the effects of preventing and treating liver diseases.

The composition for preventing or treating liver diseases and the composition for inhibiting proliferation of virus and the immune-enhancing agent, which contain any one or more of the homogeneous cell line according to the present invention, an extract thereof, a lysate thereof and a culture thereof, may be provided as a pharmaceutical composition containing any one or more of said cell line, a lysate thereof, an extract thereof and a culture thereof alone or in combination with at least one pharmaceutically acceptable carrier, excipient or diluent. The homogenous cell line, a lysate thereof, an extract thereof or a culture thereof may be contained in a pharmaceutical composition in a pharmaceutically effective amount depending on disease and its severity, the patient's age, weight, health condition and sex, the route of administration and the period of treatment, etc.

As used herein, the term "pharmaceutically acceptable" refers to a composition that is physiologically acceptable and does not cause gastric disorder, allergic reactions such as gastrointestinal disorder or vertigo, or similar reactions, when administered to humans. Examples of said carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, talc, magnesium stearate and mineral oils.

The pharmaceutical composition may additionally contain fillers, anti-aggregating agents, lubricants, wetting agents, perfumes, emulsifiers and preservatives. Also, the pharmaceutical composition of the present invention may be formulated using a method well known in the art, such that can provide the rapid, sustained or delayed release of the active ingredient after administration to mammals. The formulation may be in the form of powders, granules, tablets, emulsions, syrups, aerosols, soft or hard gelatin capsules, sterile injection solutions, sterile powders, etc.

Meanwhile, in one Example of the present invention, it was found that the homogeneous cell line according to the present invention reduces AST and ALT levels that are indicators of liver injury, suggesting that the homogeneous cell line according to the present invention has the effect of improving liver function. Thus, in another aspect, the present invention relates to a functional food for improving liver function, which contains any one or more of the ginseng cambium-derived homogeneous cell line according to the present invention, a lysate thereof, an extract thereof and a culture thereof. As used herein, the phrase "effect of improving liver function" is meant to include the effect of preventing and improving liver diseases and means improving liver function itself.

As used herein, the term "functional food" refers to a food, the functionality of which has been improved by adding thereto the homogeneous cell line of the present invention, a lysate thereof, an extract thereof or a culture thereof.

EXAMPLES

Hereinafter, the present invention will be described in further detail with reference to examples. It will be obvious to a person having ordinary skill in the art that these examples are illustrative purposes only and are not to be construed to limit the scope of the present invention.

In particular, it has been found that in the following examples, a homogeneous cell line derived from the cambium of wild ginseng, an extract thereof, and a culture thereof exhibit an effect of preventing and inhibiting liver diseases.

However, it will be obvious to a person of ordinary skilled in the art that the use of a lysate of the cell line can also obtain the same effect.

Example 1

Preparation of Homogeneous Cell Line Derived from Cambium of *Panax ginseng*

1-1: Preparation of Plant Material (1) "A" of FIG. 1(a) shows the typical feature of wild ginseng used in the present invention. In order to use the main root of wild ginseng, the main root was washed with running water to remove earth or other contaminants from the surface thereof, and the surface of the main root was washed with a liquid detergent. Then, the main root was allowed to stand under running water. The washed root tissue was placed in a sterilized flask in a clean bench and disinfected with 70% ethanol for a time ranging from about 30 seconds to about 1 minute. Then, it was rinsed with sterile distilled water and treated with a disinfectant solution containing 1-1.5% sodium hypochlorite (Junsei, Japan) for about 5-15 minutes. At this time, in order to allow the disinfectant solution to effectively penetrate into the tissue, several drops of TWEEN 20 (polyoxyethylenesorbitan monolaurate, Junsei, Japan) were added. Following this, the tissue was rinsed 3-5 times with sterile water. In order to prevent browning of the disinfected tissue, the disinfected main root was placed in antioxidant-containing BIM (browning inhibition medium) and shake-cultured for about 30 minutes to 1 hour. The cultured tissue was placed on sterile filter paper to remove water.

The composition of BIM used and the concentrations of components thereof are shown in Table 2 below.

TABLE 2

Composition of BIM and concentrations of components thereof

| Composition | Concentrations |
|---|---|
| McCown WPM salt | ¼ strength |
| Sucrose | 1%(w/v) |
| PVP(polyvinyl pyrrolidone) | 0.5%(w/v) |
| Ascorbic acid | 100 mg/l |
| Citric acid | 150 mg/l |
| Adjust to pH 5.8 | |

In Table 2, the salt is added in an amount corresponding to ¼ of the total volume.

Then, in order to prevent the above treated material from browning, the material was placed in a sterile dish containing an antioxidant-containing CS solution (cutting solution, Table 3) and peeled. Then, the material was cut into two equal parts, and each of the parts was cut to a size of 0.5-0.7 cm (width)×0.5-0.7 cm (length)×0.2-0.5 mm (thickness) in such a manner that each cut portion contained a cambium portion having active division ability. "B" of FIG. 1(a) shows the explant prepared by cutting the main root of the wild ginseng to the above size in such a manner that the explant contains the cambium.

TABLE 3

CS (cutting solution)

| Component | Concentration |
|---|---|
| PVP(Polyvinyl pyrrolidone) | 0.5%(w/v) |
| Ascorbic acid | 100 mg/l |
| Citric acid | 150 mg/l |

(2) The adventitious root of 100-year-old wild ginseng that was being maintained in a bioreactor was prepared and placed in a sterile petri dish containing the CS solution of Table 3, and an explant containing the cambium of the wild ginseng root was obtained in the same manner as described above.

1-2: Treatment of Explant Containing Cambium of Main Root of Wild Ginseng with Osmotic Agent The explant prepared in Example 1-1 was treated with osmotic stress in order to necrotize differentiated tissues (i.e., phloem, xylem, pith, etc.) and to allow only the meristem cambium to survive. The cambium-containing explant was blotted onto a preinoculation medium (medium 1, Table 4) having filter paper laid thereon, and it was placed in a flask containing 1M sucrose solution (Duchefa, Netherland) and was treated with osmotic stress in a cold state for 16-24 hours. Then, the explant was treated in 0.05M sucrose solution for 5 minutes and in 0.1M sucrose solution for 5 minutes to remove the stress caused by the high-concentration sucrose. The cambium-containing explant from which the osmotic stress has been removed was placed on a preinoculation medium (medium 1) having filter paper laid thereon to remove moisture,

TABLE 4

Composition of preinoculation medium (medium 1)

| | Composition | mM | mg/l |
|---|---|---|---|
| Macroelements | $Ca(NO_3)_2$ | 2.35 | 471.26 |
| | $NH_4NO_3$ | 5 | 400 |
| | $MgSO_4 \cdot 7H_2O$ | 1.5 | 180.54 |
| | $K_2SO_4$ | 5.68 | 990 |
| | $CaCl_2 \cdot 2H_3O$ | 0.65 | 72.5 |
| | $KH_2PO_4$ | 1.25 | 170 |

| | Composition | μM | mg/l |
|---|---|---|---|
| Microelements | $MnSO_4 \cdot 4H_2O$ | 131.94 | 22.3 |
| | $ZnSO_4 \cdot 7H_2O$ | 29.91 | 8.6 |
| | $Na_2MoO_4 \cdot 2H_2O$ | 1.03 | 0.25 |
| | $H_3BO_3$ | 100.27 | 6.2 |
| | $CuSO_4 \cdot 5H_2O$ | 1.0 | 0.25 |
| | FeNa-EDTA | 100 | 36.7 |
| Vitamin | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 2.96 | 1.0 |

1-3: Induction of Cambium-derived Homogeneous Cell Line in Explant Containing the Cambium of Wild Ginseng In order to induce a cambium-derived homogeneous cell line having the cell division ability, the explant treated with osmotic stress in Example 1-2 was transferred to a cell line induction medium (medium 2, Table 5). The composition of the medium used is shown in Table 5 below. The transferred explant was cultured in a dark condition at 22±1° C.

TABLE 5

Medium composition (medium 2) used to induce cambium-derived homogeneous cell line

| Component and condition | Concentration and condition |
|---|---|
| Salt | Full strength WPM |
| Sucrose | 3%(w/v) |
| IAA(Indole-3-acetic acid) | 2 mg/l |
| pH | 5.8 |
| Gelrite | 0.3%(w/v) |
| Ascorbic acid | 100 mg/l |
| Citric acid | 150 mg/l |

As shown in Table 6 below, in the explants transferred directly onto the homogeneous cell line-induction medium without carrying out osmotic treatment, a yellow color reaction was shown with respect to the cambium at an initial stage (2-3 days) after the transfer, and then with the passage of time, the entire explant turned yellow. The explant which has showed the yellow color reaction with respect to the cambium was subcultured in an optimal medium (medium 3) for the isolation and proliferation of a cambium-derived cell line in order to induce and proliferate the cambium-derived cell line, but the browning phenomenon became severe, and any reaction other than the browning color reaction was not shown even with the passage of time.

However, after the osmotic stress was treated and removed, it was observed as shown in Table 6 that, in the explant inoculated onto the homogeneous cell line-induction medium, a homogeneous cell line was specifically induced only in the cambium without being induced in other tissues. Specifically, it was observed that, in the transferred explant which has been treated with osmotic stress and from which the osmotic stress has been released, the cambium of the explant started to turn a light yellow after 3-7 days of the culture, and after about 7-14 days therefrom, a round cell line was induced at the portion that changed to the light yellow color. Herein, the same results were observed in both the explant containing the cambium of the true wild ginseng and the explant containing the cambium of the wild ginseng adventitious root. "C" of FIG. 1(a) shows that the homogeneous cell line having cambium-specific division ability was induced in the explant containing the cambium of wild ginseng.

Meanwhile, the explant was cultured in a 2,4-D-containing medium, which was not the homogeneous cell line induction medium and has been used in the conventional culture of *Panax ginseng*, including ginseng and wild ginseng. In this case, it was observed that the entire explant started to turn yellow after 7-10 days of the culture, and about 7-14 days therefrom, cells were induced throughout the whole cross section.

TABLE 6

Comparison of reaction between explant treated with osmotic stress and explant not treated with osmotic stress

| Treatment | Not treated | Treated for 16 hours | Treated for 20 hours | Treated for 24 hours |
|---|---|---|---|---|
| Aspect | At the initial stage after the inoculation, a yellow reaction progressed and had the tendency to spread throughout the entire explant. Then, a severe browning color reaction progressed throughout the explants including the cambium, and the induction of a homogeneous cell line, specific in the cambium, was no longer shown. | It was observed that cells were specifically induced only in the cambium. When the explant was treated with osmotic stress for varying periods of time, similar results were shown. In other words, there was no significant difference between the treatment periods. | | |

1-4: Proliferation of Isolated Homogeneous Cell Line Derived from Cambium of Wild Ginseng The cambium-derived homogeneous cell line having the ability to divide, induced in Example 1-3, was allowed to proliferate. The medium used in the proliferation was an optimal medium (Table 8) for proliferation of the cambium-derived homogeneous cell line having the ability to divide, which contained a basal salt composition (Table 7), 2,4-D in Table 8 was used for the proliferation of the homogeneous cell line derived from the cambium of the true wild ginseng, and IBA in Table 8 was used for the proliferation of the homogeneous cell line derived from the wild ginseng adventitious root.

TABLE 7

Basal salt composition of optimal medium for the isolation and proliferation of cambium-derived homogeneous cell line having the ability to divide

| Composition | | mM | mg/L |
|---|---|---|---|
| Macroelements | $CaCl_2 \cdot 2H_2O$ | 2.99 | 332.02 |
| | $KH_2PO_4$ | 1.25 | 170 |
| | $KNO_3$ | 18.79 | 1900 |
| | $MgSO_4$ | 1.5 | 180.54 |
| | $NH_4NO_3$ | 20.61 | 1650 |

| Composition | | uM | mg/L |
|---|---|---|---|
| Microelements | $CoCl_2 \cdot 6H_2O$ | 0.11 | 0.025 |
| | $CuSO_4 \cdot 5H_2O$ | 0.1 | 0.025 |
| | FeNa-EDTA | 100 | 36.7 |
| | $H_3BO_3$ | 100.27 | 6.2 |
| | KI | 5.0 | 0.83 |
| | $MnSO_4 \cdot 4H_2O$ | 100 | 16.9 |
| | $Na_2MoO_4 \cdot 2H_2O$ | 1.03 | 0.25 |
| | $ZnSO_4 \cdot 7H_2O$ | 29.91 | 8.6 |
| Vitamins | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 0.3 | 0.1 |

TABLE 8 composition of optimal medium (medium 3) for the isolation and proliferation of cambium-derived homogeneous cell line having the ability to divide

| Component and condition | Concentration and condition |
|---|---|
| Salt | Full strength MS |
| Sucrose | 3%(w/v) |
| IBA (Indole-3-butyric acid) or 2,4-D(2,4-dichlorophenoxyacetic acid) | 2 mg/L |
| pH | 5.8 |
| Gelrite | 0.3%(w/v) |
| Ascorbic acid | 100 mg/L |
| Citric acid | 150 mg/L |

As shown in "C" of FIG. 1(a), after the homogeneous cell line has been was specifically induced only in the cambium using osmotic stress treatment and medium 2, the homogeneous cell line was subcultured in medium 3 as shown in Table 8. As a result, the cambium-derived homogeneous cell line having the ability to divide continually divided and proliferated, and thus after about 10-20 days of the culture, the cambium-derived homogeneous cell line having the ability to divide could be isolated. The wild ginseng cambium-derived homogeneous cell line thus isolated was allowed to proliferate again by culturing it in the same medium. "D" of FIG. 1(a) shows that the isolated cambium-specific homogeneous cell line was allowed to proliferate in medium 3 shown in Table B.

1-5: Observation of Characteristics of Isolated Cell Line

The wild ginseng cambium-derived homogeneous cell line was placed in a flask containing the liquid medium shown in Table 9. Then, the cell line was cultured in a rotating shaker at 100 rpm in a dark condition at 25±1° C. Herein, the subculture interval was set to 2 weeks, such that the cultured cells could always maintain high vitality in the exponential growth phase-2,4-D in Table 9 was used for the proliferation of the homogeneous cell line derived from the cambium of the true wild ginseng, and IBA in Table 9 was used for the proliferation of the homogeneous cell line derived from the wild ginseng adventitious root.

Meanwhile, the ginseng cotyledon-derived callus was also cultured in medium 4 of Table 9, and the cultured callus was compared with the wild ginseng cambium-derived homogeneous cell line of the present invention.

TABLE 9

Suspension medium for *Panax ginseng* (medium 4)

| Component and condition | Concentration and condition |
|---|---|
| Salt | Full strength MS |
| Sucrose | 3%(w/v) |
| IBA (Indole-3-butyric acid) or 2,4-D(2,4-dichlorophenoxyacetic acid) | 2 mg/L |
| pH | 5.8 |

The quantification of cell aggregation was observed under an optical microscope (biological microscope CX31, Olympus, Japan). As a result, it was observed that, as shown in Table 10 below, more than 95% of cells of the true wild ginseng cambium-derived cell line treated with 2,4-D according to the present invention were present at the single cell level during suspension culture, and more than 60% of cells of the adventitious root cambium-derived cell line treated with IBA according to the present invention were also present at the single cell level, suggesting that the cell line according to the present invention is characterized in that it exists at the single cell level during suspension culture. Also, as shown in "A" of FIG. 1(b), it could be observed that the true wild ginseng cambium-derived cell line treated with 2,4-D and the adventitious root cambium-derived cell line treated with IBA were all morphologically characterized by a large number of vacuoles and were in an undifferentiated state. However, as shown in of FIG. 1(b), this morphological characteristic could not be observed in the ginseng cotyledon-derived, callus cell line.

TABLE 10

The type of cell aggregates of *Panax ginseng* long-term cultures

| Large cell aggregates | Moderate cell aggregates | Small cell aggregates | Single cell population | Explant source |
|---|---|---|---|---|
| 90% | 7% | 2% | 1% | Cotyledon |
| 0 | 0 | 5% | 95% | Cambium (2,4-D treatment) |
| 5% | 10% | 25% | 60% | Cambium (IBA treatment) |

Large cell aggregates, size higher than $1.5 \times 10^3$ μm;
Moderate cell aggregates $1 \times 10^3$ μm;
Small cell aggregates $4 \times 10^2$ μm < size < $1 \times 10^3$ μm Meanwhile, in order to examine the possibility of scale-up culture, each of the ginseng cotyledon-derived callus and the wild ginseng cambium-derived homogeneous cell line of the present invention was cultured in an airlift bioreactor (Sung-Won Cytec, Korea) having an internal volume of 3 L. The medium used in the culture was the liquid medium shown in Table 8 and was maintained in a dark condition at 25±1° C.

As a result, as shown in Table 11 below, the doubling time of the ginseng cotyledon-derived cell culture was 21 days in the flask whereas it was 28 days in the reactor. In other words, it was seen that, when cultured in the flask, the cambium-derived homogeneous cell line according to the present invention showed about 3-5-fold higher growth rate compared to cell lines derived from other tissues, and when cultured in the reactor, the cambium-derived homogenous cell line according to the present invention showed 5-9-fold higher growth rate compared to cell lines derived from tissues other than the cambium. This is believed to be because cell viability rapidly decreased due to growth ring production in the reactor, plant cell aggregation during culture, and the sensitivity of hard cell walls to shear stress.

Meanwhile, the doubling time of the true wild ginseng cambium-derived homogeneous cell culture treated with 2,4-D according to the present invention was 3-4 days in the reactor, and the doubling time of the wild ginseng adventitious root-derived homogeneous cell culture treated with IBA was 5-6 days in the reactor, which did not differ from those in the flask or was rather shortened compared to those in the flask. The cambium-derived homogeneous cell culture formed a very small growth ring area in the bioreactor, and the ring on the inner wall was simply eliminated, when a simple stimulus was applied to the bioreactor to shake the medium. Also, it was shown that the cell line of the present invention had low aggregation and contained a large number of vacuoles, and thus had low sensitivity to shear stress, so that cell viability did not decrease.

In other words, it was seen that the cambium-derived cell line according to the present invention had low sensitivity to shear stress resulting from shaking in the bioreactor for scale-up culture, and thus could be produced rapidly in large amounts in the bioreactor. Accordingly, it could be seen that the cambium-derived cell line according to the present invention had 5-9-fold lower sensitivity to shear stress compared to cell lines derived from tissues other than the cambium.

TABLE 11

Doubling time of wild ginseng cambium-derived cell line and cotyledon-derived cell line in liquid suspension culture and bioreactor

| | Doubling time (day) | |
|---|---|---|
| Explant source | flask | Bioreactor |
| Cotyledon | 21 | 28 |
| Cambium (2,4-D treatment) | 5 | 3~4 |
| Cambium (IBA treatment) | 7 | 5~6 |

Example 2

Drying of Wild Ginseng Cambium-derived Cell Line and Preparation of Extract of the Cell Line The wild ginseng adventitious root cambium-derived homogeneous cell line of Example was dried and extracted a the following manner.

(1) Preparation of Dried Cell Line
  (i) The cell line from which the culture medium has been removed was freeze-dried or hot-air-dried.
  (ii) The dried cell line was ground using a grinder.
(2) Preparation of Distilled Water Extract
  (i) 500 g of each of the cell line, from which the culture medium has been removed, and the hot-air-dried or freeze-dried cell line, was extracted in 5000 ml of distilled water with stirring at 50° C. for hours.

(ii) After completion of the extraction, the cell solution was centrifuged at 3,000 g for 10 minutes, and the supernatant was collected, thus obtaining a distilled water-soluble substance.

(iii) The obtained distilled water-soluble substance was concentrated under reduced pressure using a rotary vacuum concentrator (3) Preparation of Ethanol Extract (i) 500 g of each of the cell line, from which the culture medium has been removed, and the hot-air-dried or freeze-dried cell line, was extracted in 5000 ml of ethanol with stirring at 50° C. for 6 hours.

(ii) After completion of the extraction, the cell solution was centrifuged at 3,000 g for 10 minutes, and the supernatant was collected, thus obtaining a ethanol soluble substance.

(iii) The obtained ethanol-soluble substance was concentrated under reduced pressure using a rotary vacuum concentrator.

(4) Preparation of PBS (Phosphate Buffered Saline) Extract (i) 500 g of the freeze-dried cell line of Example 2-(1) was extracted in 5000 ml of PBS solution by heating at 80° C. for 2-3 hours using a hot water bath method.

(ii) The extract was freeze-dried and dissolved in PBS (pH7.4) to a concentration of 500 µg/µl.

Test Example 1

Examination of Antiviral Effect of *Panax Ginseng* Cambium-derived Homogeneous Cell Line Against Hepatitis B Virus In order to examine the antiviral effect of the *Panax Ginseng* cambium-derived homogeneous cell line according to the present invention against hepatitis B virus, an experiment on the inhibition of hepatitis B virus was carried out in Mibrobiology Laboratory, Department of Life Science, Suwon University.

First, the HepG2.2.25 cell line, a HepG2-derived recombinant cell line that is characterized by making and releasing HBV virion was particles, cultured in a 5% $CO_2$ bioreactor at 37° C. using DMEM10 medium (Hyclone-high glucose, 10% PBS, 10 µg/µl Gentamycin). The HepG2 cells are human liver tumor cells which are known, widely distributed and easily available, and the establishment and characteristics of the HepG2 cell line are described in U.S. Pat. No. 4,393,133. Samples of this cell line are also available from the American Type culture collection, Rockville, Md., under accession number ATCC HB 8065, and from the European collection of Animal cell Cultures, Porton Down, UK. These cells have been used as a source of various proteins, e.g., tissue factor inhibitor (TFI), also known as lipoprotein associated coagulation inhibitor (LACI), by Brose and Miletich, *Proc. Natl. Acad. Sci. USA* 84, 1886-1890 (1987), and in U.S. Pat. Nos. 4,996,852, 5,106,833 and 5,212,091. HepG2.2.15 cell is derivative of HepG2. It was prepared according to Sells et al., *Proc. Nat'l. Acad. Sci. USA* 84, 1005-1009 (1987).

Then, the HepG2.2.15 cell line was grown to a confluency of about 70% in a 24-well plate, after which the PBS extract of Example 2 (4) was added to the cell culture in the 24-well plate at a concentration of 5 mg. Also, for comparison with conventional wild ginseng tissue, a PBS extract was prepared from the freeze-dried cultured root of wild ginseng in the same manner as Example 2 (4) and added to the HepG2.2.15 cell line culture medium at the same concentration. After adding each of the PBS extract of Example 2(4) and the PBS extract of the cultured root of wild ginseng, the culture medium was replaced with DMEM2 (Hyclone-high glucose, 2% FBS, 10 µg/µl Gentamycin), and the cells were cultured in a 5% $CO_2$ bioreactor at 37° C.

The cells were cultured for 72 hours, and then, in order to measure whether HBV virion particles were produced, 5 µl of the cell culture was selected and heat-inactivated, and PCR was performed using the heat-activated cell culture as a template. As a control, a culture medium obtained by culturing the HepG2.2.15 cell line in DMEM2 without treatment with any extract was used.

A primer base sequence used to perform the PCR amplification was prepared by selecting the common portion of the HBV virus HBsAg gene. Specifically, the following primer set was used: forward primer (residue Nos. 157-179): 5'-GGGGGAATTCATGGAGAACATCACAT-CAGGATTC-3' (SEQ ID NO: 1); and backward primer (residue Nos. 814-837): 5'-GGGCTGCAGTTAAATGTATAC-CCAAAGACAAAA-3' (SEQ ID NO: 2). The DNA length between the left primer and the right primer was 750 bp. After performing the PCR amplification, each of the samples was electrophoresed on 1.0% agarose gel.

Figure 2:
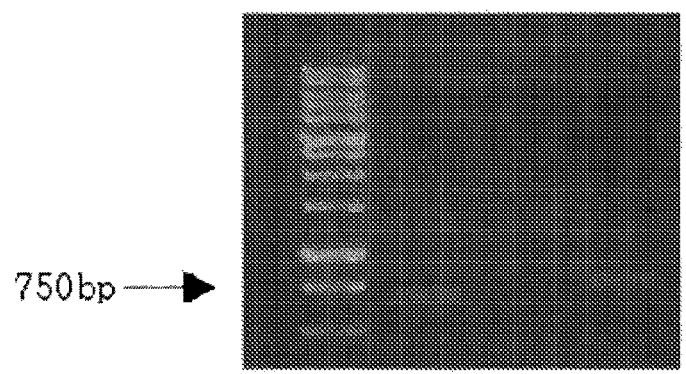
FIG. 2 is an electrophoresis photograph showing the results of comparatively observing the virus inhibitory effects of a homogeneous cell, line of the present invention and the cultured root of wild ginseng.

As a result, as shown in FIG. 2, in the control group (C) and the group (G5) treated with the freeze-dried cultured root of wild ginseng, HBsAg DNA was amplified, but in the group (G4) treated with the wild ginseng cambium-derived homogeneous cell line extract according to the present invention, HBsAg DNA was not amplified. It was believed that the reason why the FOR product was not synthesized in the group treated with the homogeneous cell line according to the present invention is that the cell line according to the present invention acted as an inhibitor to inhibit the viral production process.

Meanwhile, in order to observe the inhibitory effect of the homogeneous cell line of the present invention at various points of time, the HepG2.2.15 cell line was treated with 5 mg of the homogeneous cell line extract in the same manner as described above and cultured for each of 24 hr, 48 hr and 72 hr. Then, 5 µl of the cell culture was selected and heat-inactivated, and PCR was performed using the cell culture as a template in the same manner as described above.

As a result, as shown in FIG. 3, when PCR was performed after culturing the cells for 24 hours after treatment with the cell line extract, the HBsAg DNA amplification product was observed. However, from 48 hours after treatment with the cell line extract, the effect of inhibiting the production of the amplification product started to be observed, and after 72 hours, the amplification product was not observed. Namely, 48 hours after treatment with the cell line extract, the effect of inhibiting hepatitis B was shown.

In addition, the culture of the wild ginseng cambium-derived homogeneous cell line of Example 1 which was suspension-cultured for 14 days was treated with air stress as an elicitor for 3-5 days, A PBS extract was prepared using the cell culture according to the method of Example 2 (4), and then subjected to PCB in the same manner as described above. As a result, it was confirmed that the culture of the wild ginseng cambium-derived homogeneous cell line also exhibited an inhibitory effect against hepatitis B virus at a level similar to that shown in FIG. 3.

Test Example 2

Examination (1) of the Effect of *Panax ginseng* Cambium-derived Homogeneous Cell Line on the Prevention and Treatment of Liver Diseases In order to examine the hepatitis preventive and therapeutic effects of *Panax ginseng* cambium-derived homogeneous cell line according to the present invention, hepatitis B virus carriers and acute hepatitis patients and liver cancer patients were administered with the powder form of the dried cell line prepared in Example 2(1). 1 g of the cell line was dissolved in water and orally administered twice (morning and evening) a day.

The administration period was different depending on the patient. After the administration, HBsAg and HBeAg antigens and HBsAb, HBeAb and HBcAb antibodies were measured using an enzyme immunoassay (EIA, Enzygnost, Behringwerke, Germany) according to the manufacturer's instruction, and the quantification of hepatitis B virus (HBV) DNA was measured using a Hybrid Capture II test (HC-II, Digene Corp., Beltsville, Md., USA) according to the manufacturer's instruction. Meanwhile, AST and ALT levels were measured using a Hitachi 7600 series automatic chemical analyzer (Hitachi, Tokyo, Japan) according to the manufacturer's instruction.

The measurement results and the period of administration to each patient are shown below.

TABLE 12

Clinical case 1 (N/A: not applicable; −: negative; +: positive)

| Kim XX(female, 48) | HBsAg | HBsAb | HBcAb | 기타 |
|---|---|---|---|---|
| Before administration | + | − (<2.0) | + | |
| 7 months after administration | − (0.54) | + (270.10) | N/A | Formation of Immunity to hepatitis B |

※ The Health Promotion Center, the Korea Association of Health Promotion
HBsAg(EIA): 0-2.53 (negative), and 2.54 or more (positive);
HBsAb(EIA): 0-14.9 (negative), and 15.0 or more (positive)

As can be seen in Table 12 above, HBsAg (hepatitis B surface antigen) was positive before administration of the cell line according to the present invention, but was measured to be negative after 7 months of administration of the cell line. Also, HBsAb (hepatitis B surface antibody) was negative before administration of the cell line, but was measured to be positive after 7 months of administration of the cell line, suggesting that the s-antibody (HBsAb) was formed by administration of the homogeneous cell line according to the present invention.

The formation of the s-antibody means complete recover from hepatitis B infection, and thus it could be seen that hepatitis B was treated by administration of the cell line according to the present invention,

TABLE 13

Clinical case 2

| Lim XX (male, 38) Disease: liver cancer | HBsAg | HBsAb | Etc. |
|---|---|---|---|
| Before administration | N/A | N/A | |
| 3 months after administration | − (0.46) | + (17) | Formation of Immunity to hepatitis B |

As can be seen in Table 13 above, measurements were performed after 3 months of administration of the cell line according to the present invention. As a result, HBsAg (hepatitis B surface antigen) was measured to be negative, and HBsAb (hepatitis B surface antibody) was measured to be positive. The positivity of the s-antibody means complete recovery from hepatitis B, and thus it can be seen that the s-antibody was formed due to administration of the homogeneous cell line according to the present invention.

Accordingly, it could be seen that hepatitis B was treated by administration of the homogeneous cell line according to the present invention. Also, it could be seen that administration of the homogeneous cell line exhibited the effect of alleviating liver cancer.

TABLE 14

Clinical case 3

| Chang XX(male, 45) Disease: chronic hepatitis B with acute exacerbation (assumption) | HBsAg | HBsAb | HBeAg | HBeAb | AFP |
|---|---|---|---|---|---|
| Before administration | N/A | N/A | + (23.25) | N/A | 111.5 |
| 15 days after administration | + (3556) | + (>1000) | + (3.22) | + | 17.45 |

The time of the first judgment of carrier: the year 2000

As can be seen in Table 14 above, measurements were performed after 15 days of administration of the cell line according to the present invention. As a result, the level of HBeAg (hepatitis B e-antigen) decreased from 23.25 before administration to 3.22 after administration, indicating the proliferation of virus decreased. Meanwhile, HBeAb and HBsAb were all measured to be positive.

Thus, it could be seen that the homogeneous cell line according to the present invention had the effect of treating hepatitis B.

Meanwhile, the results of performing measurements for the above patient during the subsequent administration periods are shown below.

TABLE 15

Additional measurement for clinical case 3

| Measurement Indicator | Standard value | 45 days after administration | 2 and a half months after administration | 3 and a half months after administration | 4 and a half months after administration | 5 and a half months after administration |
|---|---|---|---|---|---|---|
| AST | 10-40 | 63 | 48 | 61 | 48 | 50 |
| ALT | 6-37 | 83 | 50 | 71 | 66 | 71 |
| HBsAg | − | +(100.00) | +(100.00) | +(3179.00) | >100.00 | +(>100.00) |
| HBsAb | +/− | +(>765) | +(>443) | +(>1000.0) | +(525) | +(399) |
| HBeAg | − | −0.73 | −0.41 | −0.17 | −0.15 | −0.35 |
| HBeAb | + | +(0.10) | +(0.10) | +(<0.10) | +(<0.10) | +(<0.10) |

As can be seen in Table 15 showing the results obtained after 45 days of administration, HBsAg and HBeAg levels decreased compared to the data before administration and after 15 days of administration as shown in Table 14 above, and HBsAb and HBeAb levels also gradually decreased after increased. However, the decreases in the antibody levels were normal ranges, and this decrease is believed to be because the levels of the antigens were significantly decreased due to administration of the homogeneous cell line according to the present invention.

Meanwhile, AST and ALT levels that are indicators of liver injury were measured. As a result, the AST and ALT levels showed fluctuation and a tendency to gradually decrease, suggesting that the homogeneous cell line according to the present invention had the effects of improving liver function and treating liver diseases.

TABLE 16

Clinical case 4

Song XX (male, 39)
Disease: hepatitis
B carrier

| | HBeAg | HBeAb | HBcAb | HBV-DNA |
|---|---|---|---|---|
| Before administration | + | − | N/A | + |
| 15 days after administration | + | − | − | + |
| 44 days after administration | − | + | − | − |

The time of the first judgment of carrier: 2006.10

As can be seen in Table 16 above, measurements were performed after 15 days of administration and 44 days of administration of the cell line. In the results of measurement after 15 days of administration, HBeAg and HBV-DNA all appeared to be positive, and HBeAb appeared to be negative, but in the results of measurement after 44 days of administration, HBeAg and HBV-DNA all appeared to be negative, and HBeAb appeared to be positive. The levels of the antigens for hepatitis virus were decreased due to administration of the homogeneous cell line according to the present invention, suggesting that the homogeneous cell line according to the present invention inhibited the proliferation of hepatitis virus. Meanwhile, it could be seen that the levels of the antibodies against hepatitis virus were increased, suggesting that the homogeneous cell line according to the present invention had an immune enhancing effect.

Accordingly, it could be seen that the homogeneous cell line according to the present invention had the effect of treating hepatitis B.

Meanwhile, the results of measurements obtained for the above patient during the subsequent administration periods are shown in Table 17 below.

TABLE 17

Additional measurement for clinical case 4

| Measurement Indicator | Standard value | Before administration | 2 and a half months after administration | 3 and a half months after administration | 4 and a half months after administration |
|---|---|---|---|---|---|
| AST | 0-37 | 146 | 34 | 29 | 26 |
| ALT | 0-40 | 47 | 27 | 26 | 21 |
| HBeAg | − | + | − | −(0.01) | −(0.01) |
| HBeAb | + | − | + | +(0.22) | +(0.24) |
| HBV-DNA | −(0.5) | + | − | −(<0.5) | −(<0.5) |

As can be seen in Table 17 above, measurements were performed after 2 and a half months of administration of the cell line. As a result, HBeAg and HBV-DNA all appeared to be negative, and HBeAb appeared to be positive. Meanwhile, the results of measuring the AST and ALT levels that are indicators of liver injury showed that the AST and ALT levels entered the normal ranges after 2 and a half months of administration, unlike the levels before administration. This suggests that the homogeneous cell line according to the present invention has the effects of improving liver function and treating liver diseases.

TABLE 18

Clinical case 5

Shin XX(female, 52)
Disease: hepatitis
B carrier

| | HBsAg | HBsAb | HBeAg | HBeAb | HBV-DNA |
|---|---|---|---|---|---|
| Before administration | + | − | + (306.60) | − | $1.0 \times 10^8$ |

TABLE 18-continued

| Clinical case 5 | | | | | |
|---|---|---|---|---|---|
| Shin XX(female, 52) Disease: hepatitis B carrier | HBsAg | HBsAb | HBeAg | HBeAb | HBV-DNA |
| 15 days after administration | N/A | N/A | + (23.60) | − | 211 |

The time of the first judgment of carrier: about 15 years ago

As can be seen in Table 18 above, measurements were performed after 15 days of administration of the cell line according to the present invention. As a result, the level of HBeAg (hepatitis B e-antigen) decreased from 306.30 before administration to 23.60 after 15 days of administration, and the HBV-DNA level significantly decreased from $1.0 \times 10^8$ before administration to 211 after administration.

This suggests that the homogeneous cell line according to the present invention has the effect of inhibiting the proliferation of hepatitis B virus.

TABLE 19

| Clinical case 6 | | | | |
|---|---|---|---|---|
| Chung XX(female, 27) Disease: hepatitis B carrier | HBeAg | HBeAb | HBV-DNA | HBcAb |
| Before administration | + (460.1) | − | N/A | N/A |
| 15 days after administration | + (301.0) | − | + ($1.0 \times 10^8$) | + (0.01) |

The time of the first judgment of carrier: the year 1992-1993

As can be seen in Table 19 above, measurements were performed after 15 days of administration of the cell line. As a result, the level of HBeAg (hepatitis B e-antigen) decreased from 460.1 before administration to 301.0 after 15 days of administration.

This suggests that the homogeneous cell line according to the present invention has the effect of inhibiting the proliferation of hepatitis B virus.

TABLE 20

| Clinical case 7 | | | | | | |
|---|---|---|---|---|---|---|
| ParkXX (male, 45) Disease: hepatitis B carrier | HBsAg | HBsAb | HBeAg | HBeAb | HBV-DNA | HBcAb (IgG) |
| Before administration | + (5292) | − (2.0) | − (0.547) | + | − (0.17) | N/A |
| 15 days after administration | + (100) | − (2.0) | − (0.01) | + | − (<0.5) | + (>0.8) |

The time of the first judgment of carrier: the year 1990

As can be seen in Table 20 above, measurements were performed after 15 days of administration of the homogeneous cell line. As a result, the level of HBsAg (hepatitis B surface antigen) decreased from 5292 before administration to 100 after 15 days of administration.

This suggests that the homogeneous cell line according to the present invention has the effect of alleviating hepatitis B.

TABLE 21

| Clinical case 8 | | | | | |
|---|---|---|---|---|---|
| Kim XX(male, 53) Disease: hepatitis B carrier | HBsAg | HBsAb | HBeAg | HBeAb | HBV-DNA |
| Before administration | + | − | − (0.42) | + | 23,889 |
| 15 days after administration | + (353.35) | − (0.0) | N/A | N/A | <2000 |

The time of the first judgment of carrier: about 20 years ago

As can be seen in Table 21 above, measurements were performed after 15 days of administration of the homogeneous cell line. As a result, the level of HBV-DNA significantly decreased from 23,889 before administration to 2000 or less after administration.

This suggests that the homogeneous cell line according to the present invention has the effect of inhibiting the proliferation of hepatitis B virus.

In the summary of the above measurement results, it can be seen that, when the *Panax ginseng* cambium-derived homogeneous cell line according to the present invention was administered for a long period of 40 days or more, the s-antibody indicating complete recovery from hepatitis B was formed, suggesting that the homogeneous cell line according to the present invention has the effects of treating hepatitis and enhancing immunity. Also, when the homogeneous cell line according to the present invention was administered for 15 days, the antigen of hepatitis B virus was measured to decrease, suggesting that the homogeneous cell line according to the present invention has the effects of inhibiting the proliferation of hepatitis B and alleviating hepatitis. In addition, it was confirmed that the homogeneous cell line according to the present invention has the effect of lowering the AST and ALT levels that are indicators of liver injury.

Accordingly, it could be seen that the *Panax ginseng* cambium-derived homogeneous cell line according to the present invention has not only the effects of preventing and treating hepatitis, but also the effects of improving liver function and preventing and treating liver diseases.

Comparative Example 1

Examination of the Effects of Wild Ginseng Adventitious Root as a Control Group on the Prevention and Treatment of Hepatitis For comparison with the hepatitis preventive and therapeutic effects of the *Panax ginseng* cambium-derived homogeneous cell line according to the present invention, hepatitis B virus carriers were administered with the dried powder of the wild ginseng adventitious root in the same manner as Example 1 above. Then, the hepatitis carriers administered for 15 days and the hepatitis carriers administered for 1 month, HBsAg and HBeAg antigens and HBsAb, HBeAb and HBcAb antibodies were measured using an enzyme immunoassay (EIA) in the same manner as Test Example 1, and the level of hepatitis virus (HBV) DNA was measured using a Hybrid Capture II test in the same manner as Test Example 1. The results of the measurements are shown in Tables 22 to 24 below.

TABLE 22

| Control case 1 | | | | | |
|---|---|---|---|---|---|
| Chung XX(male, 51) Disease: hepatitis carrier | HBsAg | HBsAb | HBeAg | HBeAb | HBV-DNA |
| Before administration | + (>250.0) | − (0.0) | + (949.63) | − | >1.0 × 10$^8$ |
| 15 days after administration | + (>250.0) | − (0.08) | + (1105.303) | − | >1.0 × 10$^8$ |

The time of the first judgment of carrier: about 40 years ago (vertical infection)

TABLE 23

| Control case 2 | | | | | |
|---|---|---|---|---|---|
| Chung XX(Male, 34) Disease: hepatitis carrier | HBsAg | HBsAb | HBeAg | HBeAb | HBV-DNA |
| Before administration | + (271.99) | − (0.0) | + (977.10) | − | 459.6 |
| 15 days after administration | + (271.02) | − (0.08) | + (911.00) | − | >1.0 × 10$^8$ |

The time of the first judgment of carrier: about 16 years ago (vertical infection)

TABLE 24

Control case 3

Yun XX(female, 34)
Disease: hepatitis
carrier

| | HBsAg | HBsAb | HBeAg | HBeAb | HBV-DNA |
|---|---|---|---|---|---|
| Before administration | + (293) | − | − (0.1) | + | − (15,000) |
| 1 month after administration | + (277) | − | − (0.58) | + | − (24,422) |

The time of the first judgment of carrier: the year 2001-2002

As can be seen in Tables 22 to 24 above, measurements were performed after administration of the wild ginseng adventitious root as a control group. As a result, when the wild ginseng adventitious root was administered for 15 days, the antigens against hepatitis virus were not substantially decreased. Also, even when it was administered for one month, the effects of reducing the levels of antigens for hepatitis virus or increasing the levels of antibodies against hepatitis virus were also insignificant.

This suggests that the effects of the *Panax ginseng* cambium-derived homogeneous cell line according to the present invention on the prevention and treatment of liver diseases were significant compared to those of the conventional *Panax ginseng*-derived cell line.

Test Example 3

Examination (2) of the Effects of *Panax ginseng* Cambium-derived Homogeneous Cell Line on the Prevention and Treatment of Liver Diseases In order to examine the hepatitis preventive and therapeutic effects of *Panax ginseng* cambium-derived homogeneous cell line according to the present invention, hepatitis B patients were administered with the dried cell line powder prepared in Example 2(1) above. Specifically, 1 g of the cell line powder was dissolved in water and orally administered twice (morning and evening) a day.

The administration period was different depending on the patient. After administration of the cell line, HBeAg and HBsAg antigens and HBeAb antibody were measured using an enzyme immunoassay (EIA, Enzygnost, Behringwerke, Germany) according to the manufacturer's instruction, and the level of hepatitis B virus (HBV) DNA was measured using a Hybrid Capture II test (HC-II, Digene Corp., Beltsville, Md., USA) according to the manufacturer's instruction. Meanwhile, AST and ALT levels were measured using a Hitachi 7600 series automatic chemical analyzer (Hitachi, Tokyo, Japan) according to the manufacturer's instruction.

The measurement results and administration period for each patient are shown below.

TABLE 25

Clinical case 9

| Chung XX (male, 48) | HBeAg | HBeAb | Etc. |
|---|---|---|---|
| Before administration | 216.86 | −12.286 | |
| 20 days after administration | 203.29 | −11.433 | |
| 2 and a half months after administration | 26.52 | +(0.704) | Formation of immunity to hepatitis B |

Normal standard value: HBeAg: −(<1.0); HBeAb: +

As can be seen in Table 25 above, measurements were performed after 20 days of administration and about 2 months and 15 days of administration of the homogeneous cell line. As a result, the level of HBeAg significantly decreased after about 2 months and 15 days of administration, suggesting that the cell line according to the present invention inhibited the proliferation of hepatitis virus. Meanwhile, the antibody against hepatitis virus appeared, suggesting the cell line according to the present invention had an immune enhancing effect against hepatitis virus.

Accordingly, it could be seen that the homogeneous cell line according to the present invention has the effect of treating hepatitis B.

TABLE 26

Clinical case 10 (N/A: not applicable; −: negative; +: positive)

| Huh XX(male, 21) | AST | ALT | HBeAg | HBeAb |
|---|---|---|---|---|
| Standard value | 0-40 | 0-40 | −(<1.0) | + |
| Before administration | 80 | 165 | N/A | N/A |
| 28 days after administration | 62 | 119 | +(5.03) | −(10.70) |
| About 2 months after administration | 70 | 169 | 5.13 | −11.33 |
| About 4 months after administration | 542 | 1463 | +(66.06) | +(0.660) |
| About 5 months after administration | 50 | 171 | N/A | N/A |
| About 6 months after administration | 24 | 36 | −(0.01) | +(0.02) |
| About 9 months after administration | 24 | 26 | −(0.39) | +(0.28) |

During 4 months of administration, the dried cell line powder was administered irregularly, however, from 4 months after administration, it was administered regularly.

As can be seen in Table 26 above, administration of the cell line was irregularly performed during 4 months after the start of administration, and then regular administration was performed. After 6 months of administration, the antigen for hepatitis virus was normally negative, and the antibody against hepatitis virus was normally positive, suggesting that the cell line according to the present invention had the effect of treating hepatitis B.

Also, in the results of measuring the AST and ALT levels, the AST and ALT levels became normal after 6 months of administration, suggesting that the cell line according to the present invention had the effects of improving liver function and treating liver diseases.

TABLE 27

Clinical case 11

| Lee XX (male, 56) | HBeAg | HBeAb | Etc. |
|---|---|---|---|
| Before administration | +(803.000) | −(3.120) | |
| About 1 month and 20 days after administration | +(290.67) | −21.134 | |
| About 2 months and 20 days after administration | +(333.86) | −(21.80) | |
| About 3 months and 20 days after administration | +(44.47) | −(1.761) | |

TABLE 27-continued

| Clinical case 11 | | | |
|---|---|---|---|
| Lee XX (male, 56) | HBeAg | HBeAb | Etc. |
| About 6 months after administration | +(10.34) | +(0.655) | Formation of immunity of hepatitis B |

Normal standard value: HBeAg: −(<1.0); HBeAb: +

As can be seen in Table 27 above, the antibody against hepatitis virus appeared after about 6 months of administration, suggesting that the cell line according to the present invention had an immune enhancing effect against hepatitis virus. Also, it could be observed that the level of HBeAg gradually decreased after administration and significantly decreased after about 6 months of administration, suggesting that the cell line according to the present invention inhibited the proliferation of hepatitis virus.

Accordingly, it could be seen that the homogeneous cell line according to the present invention has the effect of treating hepatitis B.

TABLE 28

| Clinical case 12 | | | |
|---|---|---|---|
| Kim XX (male, 32) | HBeAg | HBeAb | Etc. |
| Before administration | React(295.7) | NR(17.63) | |
| 16 days after administration | React(203.30) | NR(10.57) | |
| 2 months and 22 days after administration | React(48.21) | NR(1.71) | |
| 4 months and 14 days after administration | React(3.12) | NR(1.01) | |
| 5 months and 18 days after administration | React(1.73) | React(0.10) | Formation of immunity to hepatitis B |

Normal standard value: HBeAg: −(<1.0); HBeAb: +

As can be seen in Table 28 above, the antibody against hepatitis virus appeared after 5 months and 18 days of administration, suggesting that the cell line according to the present invention had an immune enhancing effect against hepatitis virus. Also, it could be observed that the level of HBeAg started to gradually decrease after administration and significantly decreased after 5 months and 18 days of administration, suggesting that the homogeneous cell line according to the present invention inhibited the proliferation of hepatitis virus.

Accordingly, it could be seen that the homogeneous cell line according to the present invention has the effect of treating hepatitis B.

TABLE 29

| | Clinical case 13 | | | | | | |
|---|---|---|---|---|---|---|---|
| Yun XX (female, 48) | 1 day after administration | 1 month after administration | 2 months and 12 days after administration | 4 months and 11 days after administration | 6 months and 2 days after administration | 8 months and 5 days after administration | 10 months and 16 days after administration |
| HBV-DNA (2000copies/ mL below) | 15550 | 24422 | <2000 | <2000 | 11000 | <2000 | <2000 |

As can be seen in Table 29 above, as the homogeneous cell line according to the present invention was administered, the level of HBV-DNA started to decrease and showed a stable value within the normal range after about 2 months of administration. This suggests that the homogeneous cell line according to the present invention has the effect of inhibiting the proliferation of hepatitis B virus

TABLE 30

| Clinical case 14 | | |
|---|---|---|
| Bae XX (Male, 46) | HBV-DNA | HBsAg |
| About 2 months after administration | +(2300) | +(2575) |
| About 3 months after administration | +(21000) | + |
| About 4 months after administration | +(4214) | + |
| About 5 months after administration | +(51000) | +(2351) |
| About 5 months and 10 days after administration | +(220000) | +(1933) |
| About 6 months and 11 days after administration | +(4500) | +(<1000.0) |
| About 7 months after administration | <2.000 | + |
| About 8 months after administration | <2.000 | + |
| About 9 months after administration | <2.000 | + |
| About 10 months after administration | <2.000 | +(153 above) |

Normal standard value: HBV-DNA: 2000 copies/mL below; HBsAg: negative (−)

As can be seen in Table 30 showing the results of measuring the level of HBV-DNA, the level of HBV-DNA increased and decreased, and then showed a stable value within the normal range after about 7 months of administration, suggesting that the homogeneous cell line according to the present invention had the effect of inhibiting the proliferation of hepatitis B virus. Also, the level of HBsAg antigen was positive, but showed a tendency to gradually decrease, suggesting that the cell line according to the present invention was effective in inhibiting the HBsAg antigen.

TABLE 31

| | | Clinical case 15 | | | | | |
|---|---|---|---|---|---|---|---|
| Shin XX (female, 54) | Before administration | About 1 month after administration | About 3 months after administration | About 4 months after administration | About 5 months after administration | About 6 months after administration | About 7 months after administration |
| HBV-DNA (2000copies/mL below) | 630000 | 771206 | 67000 | 12000 | <0.5 pg | 3400 | 2000 |

As can be seen in Table 31 above, as the homogeneous cell line according to the present invention was administered, the level of HBV-DNA started to decrease and showed a stable value within the normal range after about 7 months of administration. This suggests that the homogeneous cell line according to the present invention has the effect of inhibiting the proliferation of hepatitis B virus.

TABLE 32

| | Clinical case 16 | | |
|---|---|---|---|
| Kim XX (female, 42) | ALT | AST | Etc. |
| Standard value | 0-38 | 0-43 | |
| Before administration | 429 | 333 | |
| 15 days after administration | 34 | 25 | Decrease in hepatic level |

As can be seen in Table 32 showing the results of measuring the AST and ALT levels that are indicators of liver injury, the AST and ALT levels entered the normal ranges after 15 days of administration of the cell line. This suggests that the homogeneous cell line according to the present invention has the effects of improving liver function and treating liver diseases

TABLE 33

| | Clinical case 17 | | |
|---|---|---|---|
| Sohn XX (male, 49) | HBeAg | HBeAb | HBV-DNA |
| Before administration | (+) | (−) | 11900 |
| 1 month and 9 days after administration | +(7.13) | +(0.9) | <2000 |
| 4 months and 10 days after administration | −(0.86) | +(0.80) | <2000 |

Normal standard value: HBeAg: −(<1.0); HBeAb: +; HBV-DNA: 2000 copies/mL below

As can be seen in Table 33 above, after 1 month and 9 days of administration of the cell line, the antibody against hepatitis virus appeared and the level of HBV-DNA became normal, and after 4 months and 10 days of administration of the cell line, the level of the antigen became normal. This suggests that the homogeneous cell line according to the present invention has the effect of treating hepatitis B.

In the summary of the above additional measurement results for the hepatitis patients, the *Panax ginseng* cambium-derived homogeneous cell line according to the present invention showed the effects of inhibiting the proliferation of hepatitis virus while providing an immune enhancing effect against hepatitis virus. Also, the homogeneous cell line according to the present invention was confirmed to have the effect of lowering the AST and ALT levels that are indicators of liver injury. This suggests that the *Panax ginseng* cambium-derived homogeneous cell line according to the present invention has not only the effects of preventing and treating hepatitis, but also the effects of improving liver function and preventing and treating liver diseases.

Preparation Example 1

Preparation of Pharmaceutical Formulations

Formulation 1: Preparation of Tablet 100 mg of the cell line extract prepared in Example 2 was mixed with 100 mg of maize starch, 100 mg of lactose and 2 mg of magnesium stearate, and the mixture was compressed into a tablet according to a conventional tableting method.

Formulation 2: Preparation of Capsule Formulation 500 mg of the cell line extract prepared in Example 2 was filled in a soft gelatin capsule to prepare a capsule formulation.

Formulation 3: Preparation of Syrup Formulation 1 g of the cell line prepared in Example 1 was mixed with 10 g of isomerized sugar, 5 g of mannitol and a suitable amount of purified water, and the mixture was prepared into 100 ml of a syrup formulation according to a conventional method.

Formulation 4: Preparation of Injection Solution 200 mg of the cell line extract prepared in Example 2 was heated and dissolved in 200 mg of physiological saline containing polyoxyethylene hydrogenated castor oil, thus preparing an injection solution containing the extract at a concentration of 0.1%.

Preparation Example 2

Preparation of Functional Food Preparation of Functional Beverage

Preparation 1

200 mg of the cell line prepared in Example 1 was dissolved in 96 ml of water, and then 500 mg of vitamin C as a supplement, 1 g of each of citric acid and oligosaccharide as flavor enhancers and 0.05 g of sodium benzoate as a preservative were added thereto. Then, purified water was added thereto, thus preparing 100 ml of a functional beverage.

Preparation 2

200 mg of the cell line extract prepared in Example 2 Was dissolved in 96 ml of water, and then 500 mg of vitamin C as a supplement, 1 g of each of citric acid and oligosaccharide as flavor enhancers and 0.05 g of sodium benzoate as a preservative were added thereto. Then, purified water was added thereto, thus preparing 100 ml of a functional beverage.

Industrial Applicability

As described above, the homogeneous cell line, a lysate thereof, an extract thereof and a culture thereof according to the present invention are derived from a natural-derived composition and have minimized side effects compared to existing agents for treating liver diseases, and thus are safe for the human body. Also, they can increase the levels of s-antibody (HBsAb) and e-antibody (HBeAb) against hepatitis virus and inhibit the proliferation of hepatitis virus, and thus they are useful for the prevention and treatment of liver diseases. In addition, they have the effect of lowering the levels of liver injury, and thus are useful as a functional food for improving liver function.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of treating liver diseases, comprising administering a composition comprising a cell line to a patient, wherein the cell line is derived from a cambium of *Panax ginseng* by culturing cambium-containing storage root tissues of *Panax ginseng* while applying osmotic stress to the cambium-containing storage root tissue during, before or after the culture and has the following characteristics:
   a. it is in an innately undifferentiated state; and
   b. it is a homogeneous cell line.

2. The method according to claim 1, wherein the cell line is additionally characterized in that:
   a. it exists at single cell level during suspension culture;
   b. it has low sensitivity to shear stress in a bioreactor compared to cell lines derived from tissues other than the cambium of *Panax ginseng*; and
   c. it has a higher growth rate and is cultured more stably compared to the cell lines than those cell lines derived from tissues other than the cambium of *Panax ginseng*.

3. The method according to claim 1, wherein the cell line is obtained using an isolation method comprising the following steps of:
   a. obtaining a tissue containing the cambium of *Panax ginseng*;
   b. culturing the obtained cambium-containing tissue in a medium containing indole-3-acetic acid (IAA) or indole-3-butyric acid (IBA), thereby inducing a cambium-derived cell line, wherein osmotic stress is applied to the cambium-containing storage root before, during or after the culturing; and
   c. collecting the induced cambium-derived cell line.

4. The method according to claim 1, wherein the *Panax ginseng* is wild ginseng or ginseng.

5. The method according to claim 1, wherein the liver diseases is any one among hepatitis, liver cancer, liver cirrhosis, fatty liver and toxipathic liver diseases.

6. A method of improving liver function, comprising orally administering functional food containing a cell line, wherein the cell line is derived from a cambium of *Panax ginseng* by culturing cambium-containing storage root tissue of *Panax ginseng* while applying osmotic stress to the cambium-containing storage root tissue during, before or after the culture and has the following characteristics:
   a. it is in an innately undifferentiated state; and
   b. it is a homogeneous cell line.

7. The method according to claim 6, wherein the cell line is additionally characterized in that:
   a. it exists at single cell level during suspension culture;
   b. it has low sensitivity to shear stress in a bioreactor compared to cell lines derived from tissues other than the cambium of *Panax ginseng*; and
   c. it has a higher growth rate and is cultured more stably compared to the cell lines than those cell lines derived from tissues other than the cambium of *Panax ginseng*.

8. The method according to claim 6, wherein the cell line is obtained using an isolation method comprising the following steps of:
   a. obtaining a tissue containing the cambium of *Panax ginseng*;
   b. culturing the obtained cambium-containing tissue in a medium containing indole-3-acetic acid (IA) or indole- 3-butyric acid (IBA), thereby inducing a cambium-derived cell line, wherein osmotic stress is applied to the cambium-containing storage root before, during or after the culturing; and c. collecting the induced cambium-derived cell line.

9. A method of inhibiting proliferation of hepatitis virus, comprising administering a composition comprising a cell line to a host infected with hepatitis virus wherein the cell line is derived from a cambium of *Panax* by culturing cambium-containing storage root tissue of *Panax ginseng* while applying osmotic stress to the cambium-containing storage root tissue during, before or after the culture and has the following characteristics:

a. it is in an innately undifferentiated state; and
b. it is a homogeneous cell line.

10. The method according to claim 9, wherein the cell line is additionally characterized in that:

a. it exists at single cell level during suspension culture;
b. it has low sensitivity to shear stress in a bioreactor compared to cell lines derived from tissues other than the cambium of *Panax ginseng*; and
c. it has a higher growth rate and is cultured more stably compared to the cell lines than those cell lines derived from tissues other than the cambium of *Panax ginseng*.

11. The method according to claim 9, wherein the cell line is obtained using an isolation method comprising the following steps of:

a. obtaining a tissue containing the cambium of *Panax ginseng*;
b. culturing the obtained cambium-containing tissue in a medium containing indole-3-acetic acid (IAA) or indole-3-butyric acid. (IBA), thereby inducing a cambium-derived cell line, wherein osmotic stress is applied to the cambium-containing storage root before, during or after the culturing; and
c. collecting the induced cambium-derived cell line.

12. A method for increasing the level of antibody against hepatitis virus, comprising administering a composition comprising a cell line to a host infected with hepatitis virus wherein the cell line is derived from a cambium of *Panax ginseng* by culturing cambium-containing storage root tissue of *Panax ginseng* while applying osmotic stress to the cambium-containing storage root tissue during, before or after the culture and has the following characteristics:

a. it is in an innately undifferentiated state; and
b. it is a homogeneous cell line.

13. The method according to claim 12, wherein the cell line is additionally characterized in that:

a. it exists at single cell level during suspension culture;
b. it has low sensitivity to shear stress in a bioreactor compared to cell lines derived from tissues other than the cambium of *Panax ginseng*; and
c. it has a higher growth rate and is cultured more stably compared to the cell lines than those cell lines derived from tissues other than the cambium of *Panax ginseng*.

14. The method according to claim 12, wherein the cell line is obtained using an isolation method comprising the following steps of:

a. obtaining a tissue containing the cambium of *Panax ginseng*;
b. culturing the obtained cambium-containing tissue in medium containing indole-3-acetic acid (IAA) or indole-3-butyric acid (IBA), thereby inducing a cambium-derived cell line, wherein osmotic stress is applied to the cambium-containing storage root before, during or after the culturing; and
c. collecting the induced cambium-derived cell line.

* * * * *